US009554979B2

(12) United States Patent
Combs et al.

(10) Patent No.: US 9,554,979 B2
(45) Date of Patent: Jan. 31, 2017

(54) HAIR CARE COMPOSITIONS AND METHODS OF USE (71) Applicant: The Procter & Gamble Company, Cincinnati, OH (US)

(72) Inventors: Mary Jane Combs, Covington, KY (US); William David Laidig, Hamilton, OH (US); Kelly Rose Kroger-Lyons, Blanchester, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 14/825,643

(22) Filed: Aug. 13, 2015

(65) Prior Publication Data
US 2015/0342850 A1 Dec. 3, 2015

Related U.S. Application Data (62) Division of application No. 13/633,623, filed on Oct. 2, 2012, now abandoned.

(60) Provisional application No. 61/542,546, filed on Oct. 3, 2011.

(51) Int. Cl.
A61K 8/49 (2006.01)
A61K 8/34 (2006.01)
A61Q 5/00 (2006.01)
A61K 8/42 (2006.01)
A61K 8/365 (2006.01)
A61K 8/44 (2006.01)
A61K 8/25 (2006.01)
A61K 8/67 (2006.01)
A61K 8/894 (2006.01)
A61K 8/41 (2006.01)
A61Q 5/10 (2006.01)
A61Q 7/00 (2006.01)
A61K 8/81 (2006.01)

(52) U.S. Cl.
CPC ............ A61K 8/498 (2013.01); A61K 8/25 (2013.01); A61K 8/34 (2013.01); A61K 8/345 (2013.01); A61K 8/365 (2013.01); A61K 8/41 (2013.01); A61K 8/42 (2013.01); A61K 8/442 (2013.01); A61K 8/4906 (2013.01); A61K 8/4926 (2013.01); A61K 8/4946 (2013.01); A61K 8/4973 (2013.01); A61K 8/678 (2013.01); A61K 8/8152 (2013.01); A61K 8/894 (2013.01); A61Q 5/00 (2013.01); A61Q 5/10 (2013.01); A61Q 7/00 (2013.01); A61K 2800/49 (2013.01)

(58) Field of Classification Search
None
See application file for complete search history.

(56) References Cited

U.S. PATENT DOCUMENTS

| 2,118,566 | A | 5/1938 | Miles |
| 4,335,103 | A | 6/1982 | Barker et al. |
| 5,043,323 | A | 8/1991 | Bombardelli et al. |
| 5,637,606 | A | 6/1997 | Matsumoto |
| 6,239,170 | B1 | 5/2001 | Ahluwalia et al. |
| 6,414,017 | B2 | 7/2002 | Ahluwalia et al. |
| 6,465,421 | B1 | 10/2002 | Duranton et al. |
| 7,514,474 | B1 | 4/2009 | Lipkin et al. |
| 7,754,775 | B2 * | 7/2010 | Mercier ............... A61K 8/0295 424/401 |
| 7,790,768 | B2 | 9/2010 | Gan et al. |
| 8,232,317 | B2 | 7/2012 | Gan et al. |
| 2004/0141935 | A1 | 7/2004 | Styczynski et al. |
| 2005/0271692 | A1 | 12/2005 | Gervasio-Nugent et al. |
| 2006/0045926 | A1 | 3/2006 | Nimni et al. |
| 2006/0067905 | A1 | 3/2006 | Lintner et al. |
| 2008/0059313 | A1 | 3/2008 | Oblong et al. |
| 2008/0254055 | A1 | 10/2008 | Oblong et al. |
| 2009/0222350 | A1 | 9/2009 | Iwata et al. |
| 2009/0274642 | A1 | 11/2009 | Dawson, Jr. et al. |
| 2010/0137238 | A1 | 6/2010 | Gan et al. |
| 2012/0157478 | A1 | 6/2012 | Dawson, Jr. et al. |

FOREIGN PATENT DOCUMENTS

| DE | 102004041588 | | 3/2006 |
| EP | 0 640 333 | A2 | 3/1995 |
| FR | 2 643 375 | B1 | 6/1991 |
| JP | 05-97631 | | 4/1993 |
| JP | 05-117131 | | 5/1993 |
| JP | 08-003023 | | 1/1996 |
| JP | 08-073322 | | 3/1996 |
| JP | 09-263534 | | 10/1997 |
| JP | 10109920 | | 4/1998 |
| JP | 10279439 | | 10/1998 |

(Continued)

OTHER PUBLICATIONS

PCT International Search Report and Written Opinion dated Mar. 11, 2013.

(Continued)

Primary Examiner — Jennifer A Berrios
(74) Attorney, Agent, or Firm — Angela K. Haughey (57) ABSTRACT Hair care compositions including from about 0.005% to about 5% apigenin; from about 0.15% to about 12% of a solubilizing agent, wherein the solubilizing agent comprises an amine functional group; and at least about 20 weight percent of an aqueous carrier, where the composition has a pH ranging from about 3 to about 10, and methods of making the same are provided. These hair care compositions can be applied to any area of the scalp or hair where healthier hair appearance is desired.

6 Claims, 1 Drawing Sheet (56) References Cited

FOREIGN PATENT DOCUMENTS

| | | |
|---|---|---|
| JP | 2000-086510 | 3/2000 |
| JP | 2002-326931 | 11/2002 |
| JP | 2002-332218 | 11/2002 |
| JP | 2004-002264 | 1/2004 |
| JP | 2004-67573 | 3/2004 |
| JP | 2004-091354 | 3/2004 |
| JP | 2004-115465 | 4/2004 |
| JP | 2005-225849 | 8/2005 |
| JP | 2006-232820 | 9/2006 |
| JP | 2006-225310 | 8/2010 |
| WO | WO2011049629 * | 4/2011 |

OTHER PUBLICATIONS

Brocato/Beautopia, USA, Leave-In Deep Voluming Treatment, Mintel GNPD, Mar. 2007, ID677801, URL, http://www.gnpd.com/sinatra/gnpd/frontpage/.

Factors influencing the skin pH, Aus: pH and Skin Care, www.abw-verlag.de, 2007, pp. 45-49.

* cited by examiner

HAIR CARE COMPOSITIONS AND METHODS OF USE

FIELD OF THE INVENTION

The present invention relates to hair care compositions comprising one or more actives useful for regulating mammalian hair growth, increasing hair diameter, and/or delaying the appearance of gray hair, and methods of use thereof.

BACKGROUND OF THE INVENTION

Many attributes contribute to the appearance of hair considered to be attractive. For instance, hair with a full and thick appearance is very desirable. In contrast, hair with a thin appearance is not as attractive, and can even lead to a perception that the thin-haired individual is older than their chronological age. Additionally, the appearance of gray hair can also lead to the perception that an individual is older than their chronological age. Furthermore, thin hair and gray hair can be more difficult to style, and typically cannot be styled into as many hairstyles, leaving the individual frustrated and with an unkempt appearance. Because of the foregoing problems associated with thin hair and graying hair, many individuals expend great effort and time on grooming, yet still do not attain their desired hairstyle and appearance. This can lead to frustration and/or lack of confidence in his or her appearance. These problems can be experienced by both female and male consumers and at a variety of ages.

The flavone Apigenin, which is known to have antioxidant and anti-inflammatory properties, has been proposed to stimulate hair growth through various biological pathways to increase the fullness and/or thickness of hair appearance and reduce the appearance of gray hair. However, apigenin possesses poor solubility in many solvent systems and thus it is difficult to prepare compositions with efficacious quantities of solubilized apigenin. In view thereof, there is a need to provide consumers with a hair care composition that includes enhanced concentrations of apigenin.

SUMMARY OF THE INVENTION

The present invention relates to hair care compositions and methods that can help increase the appearance of fuller and/or thicker hair and/or reduce the appearance of gray hair, thus resulting in healthier and younger-looking hair. This result is achieved by increasing the diameter of hair shafts and follicles, increasing the number of hairs, reducing the emergence of gray hairs, growing longer hair, and/or having hair with less damage.

According to one embodiment, a hair care composition comprising an effective amount of a hair growth stimulating agent for the purpose of improving the appearance of the hair is provided. The hair care composition comprises from about 0.005% to about 5% apigenin; from about 0.15% to about 12% of a solubilizing agent wherein the solubilizing agent comprises an amine functional group; and at least about 20 weight percent of an aqueous carrier. In one aspect of this embodiment, the composition has a pH ranging from about 3 to about 10.

According to yet another embodiment, a process for preparing a hair care composition is provided, the method includes (i) mixing apigenin and a solubilizing agent at a temperature sufficient to allow dissolution of the apigenin in the solubilizing agent to form a premixture, wherein the weight ratio of apigenin to the solubilizing agent ranges from about 1:50 to about 1:4, (ii) combining the premixture with an aqueous carrier to form the hair care composition, and (iii) optionally, adjusting a pH of the hair care composition with acid to within a range from about 3 to about 10.

These and other features, aspects, and advantages of the claimed invention will become evident to those skilled in the art from a reading of the present disclosure.

DETAILED DESCRIPTION OF EMBODIMENTS OF THE INVENTION

While the specification concludes with the claims particularly pointing and distinctly claiming the invention, it is believed that embodiments of the present invention will be better understood from the following description. In all embodiments of the present invention, all weight percentages are by weight of the total composition, unless specifically stated otherwise. All ratios are weight ratios, unless specifically stated otherwise. All ranges are inclusive and combinable. The number of significant digits conveys neither limitations on the indicated amounts nor on the accuracy of the measurements. All numerical amounts are understood to be modified by the word "about" unless otherwise specifically indicated. All measurements are understood to be made at 25° C. and at ambient conditions, where "ambient conditions" means conditions under about one atmosphere of pressure and at about 50% relative humidity. All such weights as they pertain to listed ingredients are based on the active level and do not include carriers or by-products that may be included in commercially available materials, unless otherwise specified.

As used herein, the term "hair care compositions" are compositions that are applied to the hair and/or the skin underneath the hair, including compositions used to treat or care for the hair. Products contemplated by the phrase "hair care composition" include, but are not limited to after-shave tonics and lotions, creams, emulsions, foams, hair conditioners (rinse-off and leave-on), hair colorants, hair tonics, liquids, lotions, mousses, propellant lotions, shampoos, shave gels, temporary beard hair dyes, and the like.

"Hair growth stimulating agent" includes any material that can increase or extend an anagen phase, or provide the appearance of increasing the anagen phase of mammalian hair growth, when an effective amount of a composition containing a hair growth stimulating agent is topically applied to the desired region over a result-effective period of time. All relative terms used in connection with hair growth stimulation are understood to mean that the benefit observed is relative to that which is observed or would be expected without the exposure of a composition described herein. These observations include, but are not limited to increasing the diameter of hair shafts and follicles, increasing the number of hairs, delaying the appearance of gray hairs, growing longer hair, and/or having hair with less damage.

"Increase the appearance of fuller and thicker hair" means the diameters of hair follicles and/or shafts in the subject region of hair (e.g., scalp) are increased by a statistically significant amount, when an effective amount of a composition of the present invention is topically applied to the desired region over a result-effective period of time.

"Delay the appearance of gray hair" means the rate of gray hair emerging is delayed. It is accepted that canities (i.e., natural whitening or graying of the hair) is associated with a decrease in melanin in the hair shaft. The onset or degree of canities is associated with aging, and thus the delaying or decreasing the appearance of gray hair provides a younger looking appearance. The rate of gray hair emergence can be measured by visual observation and by the method described in Japanese patent application 2005-296352A assigned to Shiseido. The counting method consists of designating a 50 mm×10 mm area on either side of the frontal scalp and collecting all the hairs within the area and counting 1000 hairs cut from the area. Gray hairs and pigmented hairs are both counted. The process is repeated monthly, or as desired, and the percent of gray hairs is calculated.

"Mammalian hair," as referenced herein, includes hair on any part of the body of a mammal, and can include but is not limited to facial, cranial, or body hair. For instance, it can include hair on the scalp, head, neck, beard, moustache, eyebrows and sideburns hair.

The term "topical application," as used herein, means to apply or spread the compositions of the present invention onto the surface of the keratinous tissue from which the hair to be affected grows.

The term "dermatologically-acceptable," as used herein, means that the compositions or components thereof so described are suitable for use in contact with mammalian keratinous tissue without undue toxicity, incompatibility, instability, allergic response, and the like.

The term "effective amount," as used herein, means an amount of a compound or composition sufficient to increase the diameter of the shafts in the subject region of hair by a statistically significant amount, to increase the hair density (number of hairs per area) by a statistically significant amount, and/or to delay the appearance of gray hair by a statistically significant amount.

The term "solubilizing agent," as used herein means a solvent or solvent-based solution that solubilizes the hair growth stimulating agents disclosed herein.

As used herein, "apigenin" includes salts or complexes thereof. Exemplary apigenin salts include amine salts.

Briefly, as is commonly known by those skilled in the art of the instant disclosure, the hair cycle consists of three phases. The first phase, or growth phase, is known as anagen and lasts, on average, between three and four years. The second phase consists of discontinued growth over a period of two to three weeks. This phase is called catagen. The last phase, called telogen, is the phase where the hair falls out. This phase occurs fairly slowly, over the course of three to four months, as the bulbar zone of the hair follicle regresses and the hair shaft detaches and is expulsed towards the surface of the skin.

In accord with one embodiment of the present invention, a hair care composition comprising apigenin, and optionally one or more hair growth stimulating agents, is applied to the scalp and/or the base of the hair on the scalp, to increase the appearance of healthier and younger-looking hair. Applicants have found that a topical application of one or more hair growth stimulating agents to regions where the appearance of more hair is desired can actually improve the appearance of the region by having an appearance of thicker and/or fuller hair and/or delay the appearance of gray hair.

Although not wishing to be limited by theory, it is believed that topical application of various hair growth stimulating agents can: (1) interrupt or inhibit an inflammatory cycle at the hair follicles, which in turn may extend the anagen phase of the follicles; (2) stimulate aquaporin 3 ("AQP3") up-regulators, which in turn may result in thicker hair shafts and follicles; and/or (3) stimulate the production of melanin in hair melanocytes, which in turn may delay the emergence of gray hair. Accordingly, the topical application of the hair care compositions may also help to slow the rate in which hair leaves the anagen phase, stimulate AQP3 up-regulators, delay the appearance of gray hair, or combinations thereof. The increase in the diameter of the hair shafts and follicles leads to the appearance of hair that is thicker and fuller. Furthermore, the topical application can lead to the appearance of younger looking hair, since hair diameter is known to decrease with one's chronological age and the appearance of gray hair can be delayed.

The topical application of a hair care composition of present invention can aid in lengthening the anagen phase. The lengthening of the anagen phase can be achieved by either blocking the transition from anagen phase to telogen phase or by inhibiting the transition from anagen phase to telogen phase. The hair follicles are in a growing phase (anagen) or in a resting phase (telogen). Follicles are predominately in the anagen phase. The anagen phase may typically last for approximately 2 to 10 years, with an average duration of about 3 to 4 years that can vary depending on a variety of factors. Conversely, the telogen phase is much shorter and may typically last for about 3 to 4 months. In general, a person will have approximately 94% of the follicles in anagen phase and 6% of the follicles in telogen phase. Each month approximately 2% of the follicles leave anagen phase and transition to telogen phase and at the same time approximately 2% of the follicles leave telogen phase and transition to anagen phase. With the application of the hair care compositions of the present invention, the approximately 2% of the follicles leaving anagen phase can be either blocked or delayed resulting in an increased percent of hair follicles in anagen phase. The increase in the amount of follicles in anagen phase increases the hair density on the head. It is believed that the length of the anagen phase can be increased from about 2 weeks to about 2.5 months. The increase in hair density (number of hair on a certain area of the scalp) can be measured. In one embodiment of the present invention, the hair density will increase by about 2 hairs/cm$^2$, preferably by about 3 hairs/cm$^2$, and in some embodiments greater than 4 hairs/cm$^2$. The benefits of the increased anagen phase, hair density, and hair diameter and the delay of gray appearance will result in a person's hair looking from 3 or more years younger.

A. Hair Care Compositions

In one aspect, the present invention provides hair care compositions that can be used to increase the appearance of thicker and fuller hair. The hair care composition comprises at least one hair growth stimulating agent. According to embodiments of the present invention, the hair growth stimulating agent comprises a flavonoid compound, apigenin (which is also known as 4',5,7-trihydroxyflavone or 5,7-dihydroxy-2-(4-hydroxyphenyl)-4H-1-benzopyran-4-one) in a safe and effective amount. The hair care composition further includes a solubilizing agent having an amine functional group contained therein, and an aqueous carrier, wherein the composition has a pH ranging from about 3.0 to about 10. Optionally, the hair care compositions can further comprise other dermatologically-acceptable additives and/or any desired suitable optional ingredients.

1. Apigenin

The hair care composition of the present invention includes the flavonoid, apigenin, which is a nonmutagenic citrus bioflavonoid present in many types of plants and vegetables. Examples include, but are not limited to, grapefruit, parsley, thyme, chamomile, apples, celery, basil, oregano, tarragon, cilantro, yarrow, kelp, camellia, and passion flower. Although apigenin can be found in many of plants and vegetables in low quantities along with many other flavonoids, catechins, and other naturally-occurring compounds, the total concentration of apigenin in these materials varies greatly and there may not be enough apigenin present in these materials to be useful for the present invention. As such, for the present invention, the apigenin is in a purified state and substantially free of other compounds. As used herein, "substantially-free of other compounds" means that the apigenin is at least 50 wt % pure. For example, according to one embodiment, the apigenin may at least 90 wt % pure, at least 95% pure, or at least 98% pure. For the present invention, the apigenin itself must be present in an amount of at least 0.005% based on the total composition. The apigenin may be present in amount of greater than about 0.1%, 0.15%, 0.2%, 0.25%, 0.3%, 0.4%, 0.5%, 0.7%, 0.9%, 1%, 2%, 3%, or 4%. The apigenin is typically present in an amount of less than about 5%, 4%, 3%, 2.5%, 2%, 1.8%, 1.6%, 1.5%, 1.4%, 1.3%, 1.2%, 1%, 0.9%, 0.8%, 0.7%, 0.6%, 0.5%, 0.4%, 0.3%, 0.2%, or 0.1%.

2. Solubilizing Agent

Apigenin is solid in its pure form and is practically insoluble (i.e., a solubility of less than 1 mg/ml) in water and nearly all solvents suitable for pharmaceutical, cosmetic, and food additive formulations. As such, one major obstacle for formulators is the need for apigenin to be provided from a stock solution (i.e., a premixture) utilizing a solubilizing agent that is compatible with the base formulation. The choice of such solubilizing agents is not readily apparent. For example, while apigenin is known to be soluble in basic aqueous solutions, apigenin precipitates from solution upon adjusting the pH with acid. As such, another additional consideration is the ability of the solubilizing agent to assist with maintaining a stable hair care composition within the desired pH range. Thus, in another aspect of the present invention, a method is provided for selecting ideal solubilizing agents for solubilizing apigenin to facilitate its incorporation into many different products particularly those in fluid form such as a liquid, a paste, a gel or a cream. Of course, the methods described herein would also be applicable to other practically insoluble flavonoids (e.g., luteolin) and other practically insoluble hair growth stimulating agents.

The solvents selected for the solubilization method of this embodiment are based upon solubility parameters and cohesion properties explained by Charles Hansen in "Hansen Solubility Parameters: A User's Handbook" by Charles M. Hansen, CRC Press (2007) and in "The CRC Handbook and Solubility Parameters and Cohesion Parameters," edited by Allan F. M. Barton (1999). Each material is defined by three points in 3D space and these three points are known as the Hansen Solubility Parameters (HSP) which may be defined as follows.

Solubility parameters are theoretically calculated numerical constants which are a useful tool in predicting the ability of a solvent material to dissolve a particular solute. When the solubility parameters of a solvent falls within the solubility parameter range of a solute, i.e., the material to be dissolved, solubilization of the solute is likely to occur. There are three Hansen empirically- and theoretically-derived solubility parameters, a dispersion-force component ($\delta_D$), a polar or dipole interaction component ($\delta_P$) and a hydrogen-bonding component ($\delta_H$). Each of the three parameters (i.e., dispersion, polar and hydrogen bonding) represents a different characteristic of solvency, or solvent capability. In combination, the three parameters are a measure of the overall strength and selectivity of a solvent. The Total Hansen solubility parameter, which is the square root of the sum of the squares of the three parameters mentioned previously, provides a more general description of the solvency of the solvents. Individual and total Solubility Parameter units are given in $MPa^{0.5}$.

Solubility parameters for a material may then be plotted in a normal three-dimensional graph. From the location ($\delta_D$, $\delta_P$, $\delta_H$), a radius is projected to form a sphere which encompasses a region of solubility such that any solvent whose parameters reside within this space should dissolve the solute in question. The distance between the HSP coordinate of material 1 (i.e., the solute) to the HSP coordinates of material 2 (solvent) is designated herein as Ra. The 3D distance, Ra, is defined by the equation:

$$Ra^2 = 4(\delta_{D1} - \delta_{D2})^2 + (\delta_{P1} - \delta_{P2})^2 + (\delta_{H1} - \delta_{H2})^2$$

HSPs and the solubility sphere for apigenin are optimized using the fitting method in the software HSPiP version 3.1.06 from Charles M. Hansen Consulting, Hørsholm, Denmark, hansen-solubility.com. Qualitative experimental solubilities for apigenin in 32 diverse potential solvents are determined using the scoring system at the bottom of Table 1. In the fitting function within HSPiP, solvents with scores of 1 and those with scores of 2-5 are categorized as "good" and "bad" solvents, respectively. Because the fitting procedure in HSPiP does not yield a unique value for HSPiP, the default fitting algorithm is run 50 times and the following procedure is used to identify the best HSP values from this set:

1. Because the radius can be unbounded, fits with radii larger than 95% of the radius distribution are removed from these 50 trials ($\leq 8.5$ $MPa^{0.5}$).
2. Determine the ranges for $\delta_D$, $\delta_P$, $\delta_H$ for the remaining fits.
3. Locate the fit closest to this point using the Ra equation above.
4. Chose the values for $\delta_D$, $\delta_P$, $\delta_H$ from Step 2 for the HSP's and the value of Ra from Step 3 for the radius.

Using this protocol, apigenin HSP values and solvent radius are determined to be $\delta_D = 18.7$, $\delta_P = 13.5$, $\delta_H = 13.9$ and $Ra = 6.8$ (all in $MPa^{0.5}$). This sphere defines the initial region encompassing solvents into which apigenin will be soluble. (Note HSPiP v. 3.1.06 is used herein to determine all HSPs by 1) lookup if available within the program's internal database; 2) estimation if not in the database using the Y-MB method; or 3) via the procedure described above (apigenin only).)

TABLE 1

Solvents Used to Determine HSP Values for Apigenin With Their Solubility Scores and HSPs

| Solvent | CAS # | δD | δP | δH | Score[a] |
|---|---|---|---|---|---|
| Acetone | 67-64-1 | 15.5 | 10.4 | 7 | 5 |
| Acetonitrile | 75-05-8 | 15.3 | 18 | 6.1 | 5 |
| 1-Butanol | 71-36-3 | 16 | 5.7 | 15.8 | 4 |
| n-Butyl Acetate | 123-86-4 | 15.8 | 3.7 | 6.3 | 5 |
| n-Butyl Acrylate | 141-32-2 | 15.6 | 6.2 | 4.9 | 5 |
| gamma-Butyrolactone (GBL) | 96-48-0 | 18 | 16.6 | 7.4 | 4 |
| Carbon Tetrachloride | 56-23-5 | 17.8 | 0 | 0.6 | 6 |
| Chloroform | 67-66-3 | 17.8 | 3.1 | 5.7 | 5 |
| Cyclohexane | 110-82-7 | 16.8 | 0 | 0.2 | 6 |
| Cyclohexanol | 108-93-0 | 17.4 | 4.1 | 13.5 | 4 |
| Cyclohexanone | 108-94-1 | 17.8 | 8.4 | 5.1 | 4 |

TABLE 1-continued

Solvents Used to Determine HSP Values for Apigenin
With Their Solubility Scores and HSPs

| Solvent | CAS # | δD | δP | δH | Score[a] |
|---|---|---|---|---|---|
| Diacetone Alcohol | 123-42-2 | 15.8 | 8.2 | 10.8 | 4 |
| Diethanolamine | 111-42-2 | 17.2 | 7 | 19 | — |
| Dimethyl Formamide (DMF) | 68-12-2 | 17.4 | 13.7 | 11.3 | 1 |
| Dimethyl Sulfoxide (DMSO) | 67-68-5 | 18.4 | 16.4 | 10.2 | 1 |
| 1,4-Dioxane | 123-91-1 | 17.5 | 1.8 | 9 | 5 |
| Ethyl Acetate | 141-78-6 | 15.8 | 5.3 | 7.2 | 5 |
| Hexane | 110-54-3 | 14.9 | 0 | 0 | 6 |
| Methanol | 67-56-1 | 14.7 | 12.3 | 22.3 | 4 |
| Methyl Ethyl Ketone (MEK) | 78-93-3 | 16 | 9 | 5.1 | 5 |
| N-Methyl Formamide | 123-39-7 | 17.4 | 18.8 | 15.9 | 1 |
| Methyl Isobutyl Ketone (MIBK) | 108-10-1 | 15.3 | 6.1 | 4.1 | 5 |
| N-Methyl-2-Pyrrolidone (NMP) | 872-50-4 | 18 | 12.3 | 7.2 | 1 |
| 2-Phenoxy Ethanol | 122-99-6 | 17.8 | 5.7 | 14.3 | 4 |
| 2-Propanol | 67-63-0 | 15.8 | 6.1 | 16.4 | 4 |
| Propylene Carbonate | 108-32-7 | 20 | 18 | 4.1 | 5 |
| Propylene Glycol Monomethyl Ether | 107-98-2 | 15.6 | 6.3 | 11.6 | 2 |
| Propylene Glycol Monomethyl Ether Acetate | 108-65-6 | 15.6 | 5.6 | 9.8 | 5 |
| Tetrahydrofuran (THF) | 109-99-9 | 16.8 | 5.7 | 8 | 4 |
| Toluene | 108-88-3 | 18 | 1.4 | 2 | 6 |
| p-Xylene | 106-42-3 | 17.8 | 1 | 3.1 | 6 |
| Dichloromethane | 75-09-2 | 17 | 7.3 | 7.1 | 5 |

[a]Scoring System 1 = Completely Dissolved 2 = Very Swollen 3 = Swollen 4 = Slightly Swollen 5 = Hardly Swollen 6 = Not touched — = Assignment Unclear Independent, numerical estimates of apigenin solubility may also be computed using COSMOtherm software, version C21_0111_a (COSMOlogic GmbH & Co. KG, Leverkusen, Germany, www.cosmologic.de.) These estimates are used to ascertain whether the approximation that a spherical region in HSP space divides the space into "good" solvents (inside the sphere) and "bad" solvents (outside the sphere). Log $10(X_{sol})$ may be computed for the same 32 solvents used in the experimental solubility determination described above where $X_{sol}$ is the mole fraction solubility (moles of solute/total moles). The following procedure is used to include apigenin and these solvents in COSMOtherm calculations:

1. 3D conformers for each compound are generated using the program Concord (R. S. Pearlman, "Concord," distributed by Tripos International, St. Louis, Mo., 63144, USA, tripos.com).
2. These conformers are PM3 minimized and each followed by both gas-phase and infinite dielectric COSMO BP86-TZVP minimizations.
3. The BP86-TZVP energies and COSMO charge densities are used as input to the COSMOtherm solubility module.

Log $10(X_{sol})$ is regressed against the 3 sets of HSP values $\delta_D$, $\delta_P$, $\delta_H$ and their cross products. Only $\delta_P$, $\delta_H$ and $\delta_P \times \delta_H$ are significant, which implies that dispersion is not a very important solubility parameter for apigenin. As a consequence, the spherical region is actually more similar to a cylindrical region. For solubility >5% in the selected solvents, the range of $\delta_D$ (dispersibility) is about 12-22 $(MPa)^{0.5}$ with the polar and hydrogen bonding components ($\delta_P$ and $\delta_H$) falling approximately within a 6.8 $(MPa)^{0.5}$ radius around, $\delta_P=13.5$ $(MPa)^{0.5}$, $\delta_H=13.9$ $(MPa)^{0.5}$.

Non-limiting examples of solubilizing agents, which have suitable Hansen Solubility Parameters and may be used to solubilize apigenin include triethanolamine (CAS No. 102-71-6); diethanolamine (CAS No. 203-868-0); ethanolamine (CAS No. 141-43-5); N-methylformamide (CAS No. 123-39-7); 2-dimethylaminoethanol (CAS No. 203-542-8); 2-dimethylamino-2-propanol (108-16-7); ethylenediamine (CAS No. 107-15-3); 2-amino-2-methyl-1-propanol (CAS No. 124-68-5); laurocapram (CAS No. 59227-89-3); and dimethyl capramide (Spectrasolv, CAS No. 14433-76-2). Non-limiting examples of solvents, which have suitable Hansen Solubility Parameters and may be used in combination with one or more solubilizing agents include dipropyleneglycol (CAS No. 110-98-5); propylene glycol (Hydrolite™ 5, CAS No. 5343-92-0); butylene glycol (CAS No. 107-88-0); 1,4-butanediol (CAS No. 110-63-4); 3-allyloxy-1,2-propanediol (CAS No. 123-34-2); dipropylene glycol n-butyl ether (CAS No. 29911-28-2); 1,2-hexanediol (CAS No. 6920-22-5); dimethyl isosorbide (Arlasolve™ CAS No. 5306-85-4); ethanol (CAS No. 64-17-5); 1,3-butanediol (CAS No. 107-88-0); 1,3-propanediol (CAS No. 504-63-2); 2,2'-thiodiethanol (CAS No. 111-48-8); and 1,6-hexanediol (CAS No. 629-11-8). Table 2 provides a summary of various solubilizing agents and solvents and their respective HSP values, along with experimentally observed apigenin solubility.

TABLE 2

Exemplary solubilizing agents and solvents, and their respective Hansen Solubility Parameter (HPS) values.

| Solubilizing Agent | CAS | δD | δP | δH | Total HSP | Ra | Experimental solubility |
|---|---|---|---|---|---|---|---|
| dipropyleneglycol | 110-98-5 | 16 | 8.7 | 21.3 | 28.0 | 1.5 | 2.19% at 115 C. |
| propylene glycol | 5343-92-0 | 16.1 | 8.0 | 16.9 | 24.7 | 1.2 | 0.62% at 100 C. |
| butylene glycol | 107-88-0 | 16.5 | 8.1 | 20.9 | 27.8 | 1.5 | 1.52% at 98 C. |
| 1,4-butanediol | 110-63-4 | 16.6 | 11.0 | 20.9 | 28.9 | 1.3 | 1.0% at 110 C. |
| 3-allyloxy-1,2-propanediol | 123-34-2 | 16.2 | 8.5 | 16.2 | 24.4 | 1.1 | 1.0% at 120 C. |
| dipropylene glycol n-butyl ether | 29911-28-2 | 15.7 | 6.5 | 10.0 | 19.7 | 1.5 | 0.6% at 90 C. |
| 1,2-hexanediol | 6920-22-5 | 16.0 | 7.4 | 16.7 | 24.3 | 1.3 | 0.4% at 90 C. |
| dimethyl isosorbide | 5306-85-4 | 17.6 | 7.1 | 7.5 | 20.4 | 1.4 | 1.54% at 100 C. |
| Ethanol | 64-17-5 | 15.8 | 8.8 | 19.4 | 26.5 | 1.4 | 0.32% at 21 C. and 50 C. |
| triethanolamine | 102-71-6 | 17.3 | 7.6 | 21.0 | 28.2 | 1.4 | 12.7% at 165 C. |
| diethanolamine | 108-01-0 | 16.1 | 9.2 | 14.0 | 23.2 | 1.0 | 20.25% at 128 C. |
| ethanolamine | 141-43-5 | 17.0 | 15.5 | 21.0 | 31.1 | 1.2 | 20.31% at 76 C. |
| 1,3-butanediol | 107-88-0 | 16.5 | 8.1 | 20.5 | 27.5 | 1.4 | 1.52% at 98 C. |
| N-methylformamide | 123-39-7 | 17.4 | 8.8 | 15.9 | 25.2 | 0.8 | Ppt upon cooling |
| 2,2'-thiodiethanol | 111-48-8 | 17.3 | 8.8 | 19.8 | 27.7 | 1.2 | 0.47% at 103 C. |
| 2-dimethylaminoethanol | 108-01-0 | 16.1 | 9.2 | 14.0 | 23.2 | 1.0 | 19.95% at 29 C. |
| 2-dimethylamino-2-propanol | 108-16-7 | 16.6 | 19.4 | 18.0 | 31.2 | 1.2 | 20.18% at 21 C. |

TABLE 2-continued

Exemplary solubilizing agents and solvents, and their respective Hansen Solubility Parameter (HPS) values.

| Solubilizing Agent | CAS | $\delta_D$ | $\delta_P$ | $\delta_H$ | Total HSP | Ra | Experimental solubility |
|---|---|---|---|---|---|---|---|
| ethylenediamine | 107-15-3 | 16.6 | 8.8 | 17.0 | 25.3 | 1.0 | 20.03% at 28 C. |
| 2-amino-2-methyl-1-propanol | 124-68-5 | 15.7 | 8.0 | 15.5 | 23.5 | 1.2 | 20.03% at 71 C. |
| 1,6-Hexanediol | 629-11-8 | 15.7 | 8.4 | 17.8 | 25.2 | 1.3 | 4.12% at 137 C. |
| 1,3-propanediol | 504-63-2 | 16.8 | 13.5 | 23.2 | 31.7 | 1.5 | 0.73% at 100 C. |
| Laurocapram[a] | 59227-89-3 | 17.0 | 4.4 | 3.0 | 17.8 | 2.1 | 13.0% at 21 C. |
| Dimethyl capramide[a] | 14433-76-2 | 16.6 | 6.7 | 5.7 | 18.8 | 1.7 | 16.0% at RT |

[a]Not in database - estimated using Y-MB method

According to one aspect of the solubilizing agent, the solubilizing agent includes at least one amine functional group therein. Accordingly, the amine functional group can be selected from a primary amine, a secondary amine, a tertiary amine, or an amide. According to one example, the solubilizing agent includes a plurality of amine functional groups. According to another example, the solubilizing agent includes a hydroxyl functional group. According to another example, the solubilizing agent includes a plurality of hydroxyl functional groups. According to another example, the solubilizing agent includes at least one amine functional group and at least one hydroxyl functional group. For example, the solubilizing agent can include an amine functional group and 2 or 3 hydroxyl functional groups. In one example, the solubilizing agent is triethanolamine. In another example, the solubilizing agent is dimethylcapramide.

According to another embodiment, the hair care composition may include a plurality of solubilizing agents. For example, it is envisioned that synergistic combinations of solubilizing agents may be utilized to achieve enhance solubility characteristics and thereby enable increased concentration levels of apigenin and other additional hair growth stimulating agents.

According to another embodiment, the solubilizing agent itself is present in an amount of at least 0.15% based on the total composition. The solubilizing agent may be present in amount of greater than about 0.2%, 0.5%, 1%, 1.5%, 2%, 3%, 4%, 5%, 6%, 8%, 10%, or 12%. The solubilizing agent is typically present in an amount equal to or less than about 12%, 10%, 8%, 6%, 5%, 4%, 3%, 2%, 1.5%, 1%, 0.5%, 0.2%, or 0.15%.

According to yet another embodiment, the hair care composition may further include one or more solvents, such as dipropyleneglycol, propylene glycol, butylene glycol, 1,4-butanediol, 3-allyloxy-1,2-propanediol, dipropylene glycol n-butyl ether, 1,2-hexanediol, dimethyl isosorbide, ethanol, 1,3-butanediol, 1,3-propanediol, 2,2'-thiodiethanol, and 1,6-hexanediol, or combinations thereof.

According to yet another embodiment, the hair care composition may further include one or more additional hair growth stimulating agents, such as those disclosed in U.S. Patent Application Publication No. 2010/0120871. Accordingly, non-limiting examples of additional hair growth stimulating agents include indole compounds, xanthine compounds, vitamin $B_3$ compounds, panthenol compounds, and derivatives thereof.

A. Indole Compounds

The hair care compositions can further include an indole compound. As used herein, "indole compound" means one or more indoles, derivatives thereof, mixtures thereof, or salts thereof. Accordingly, the composition may include from about 0.1% to about 10% of the indole compound, from about 0.5% to about 5% of the indole compound, or from about 1% to about 2% of the indole compound, for example, wherein the percentage is a weight percentage based on the total weight of the final hair care composition.

B. Xanthine Compounds

The hair care compositions can further include a xanthine compound. As used herein, "xanthine compound" means one or more xanthines, derivatives thereof, and mixtures thereof. Xanthine compounds that can be useful herein include, but are not limited to, caffeine, xanthine, 1-methylxanthine, theophylline, theobromine, derivatives thereof, and mixtures thereof. Accordingly, the composition may include from about 0.1% to about 10% of the xanthine compound, from about 0.5% to about 5% of the xanthine compound, or from about 1% to about 2% of the xanthine compound, for example, wherein the percentage is a weight percentage based on the total weight of the final hair care composition. For example, the hair care composition may further include about 0.75% of caffeine.

C. Vitamin $B_3$ Compounds

The hair care compositions can further include a vitamin B3 compound. As used herein, "vitamin $B_3$ compound" means nicotinic acid, niacinamide, nicotinyl alcohol, derivatives thereof, and mixtures thereof. The vitamin $B_3$ compound may be included as the substantially pure material, or as an extract obtained by suitable physical and/or chemical isolation from natural (e.g., plant) sources. Accordingly, the composition may include from about 0.1% to about 25% of the vitamin $B_3$ compound; from about 0.5% to about 15% of the vitamin $B_3$ compound; or from about 3.5% to about 7.5% of the vitamin $B_3$ compound, for example, wherein the percentage is a weight percentage based on the total weight of the final hair care composition. For example, the hair care composition may further include about 2.5% of vitamin $B_3$.

D. Panthenol Compounds

The hair care compositions can further comprise a panthenol compound. As used herein, the term "panthenol compound" includes panthenol, one or more pantothenic acid derivatives, and mixtures thereof. Non-limiting examples of panthenol compounds include D-panthenol ([R]-2,4-dihydroxy-N-[3-hydroxypropyl)]-3,3-dimethylbutamide), D,L-panthenol, pantothenic acids and their salts (e.g., the calcium salt), panthenyl triacetate, royal jelly, panthetine, pantotheine, panthenyl ethyl ether, pangamic acid, pantoyl lactose, Vitamin B complex, or mixtures thereof. Accordingly, the composition may include from about 0.01% to about 5% of the panthenol compound; from about 0.03% to about 3% of the panthenol compound; from about 0.05% to about 2% of the panthenol compound; or from about 0.1% to about 1% of the panthenol compound, for example, wherein the percentage is a weight percentage based on the total weight of the final hair care composition. For example, the hair care composition may further include about 0.15% of panthenol.

According to another aspect of the present invention, the hair care compositions may be free of oleanolic acid and/or biotinyl-GHK, which is contrary to that described in U.S. Patent Application No. 20060067905.

3. Carrier

According to another aspect of the present invention, the hair care compositions further include at least about 20 weight percent of an aqueous carrier. According to one embodiment, the aqueous carrier may be prepared from demineralized or distilled water, for example. Other acceptable carriers that may be used in the aqueous carrier include, but are not limited to alcohol compounds, such as ethanol. According to one embodiment, the composition comprises alcohol, dipropylene glycol, and/or water.

The hair care compositions have a pH ranging from about 3.0 to about 10, which may be measured by taking a direct pH measurement using a standard hydrogen electrode of the composition at 25° C. Accordingly, the pH of the hair care composition may be within the range from about 6 to about 9, for example.

4. Optional Ingredients

The compositions of the present invention can also additionally comprise any suitable optional ingredients as desired. For example, the composition can optionally include other active or inactive ingredients.

The compositions may include other common hair ingredients such as pyrithione zinc, minoxidil, silicones, conditioning agents, and other suitable materials. The CTFA Cosmetic Ingredient Handbook, Tenth Edition (published by the Cosmetic, Toiletry, and Fragrance Association, Inc., Washington, D.C.) (2004) (hereinafter "CTFA"), describes a wide variety of nonlimiting materials that can be added to the composition herein. Examples of these ingredient classes include, but are not limited to: abrasives, absorbents, aesthetic components such as fragrances, pigments, colorings/colorants, essential oils, skin sensates, astringents, etc. (e.g., clove oil, menthol, camphor, eucalyptus oil, eugenol, menthyl lactate, witch hazel distillate), anti-acne agents, anti-caking agents, antifoaming agents, antimicrobial agents (e.g., iodopropyl butylcarbamate), antioxidants, binders, biological additives, buffering agents, bulking agents, chelating agents, chemical additives, colorants, cosmetic astringents, cosmetic biocides, denaturants, drug astringents, external analgesics, film formers or materials, e.g., polymers, for aiding the film-forming properties and substantivity of the composition (e.g., copolymer of eicosene and vinyl pyrrolidone), opacifying agents, pH adjusters, propellants, reducing agents, sequestrants, rheology modifiers, hair conditioning agents, and surfactants.

In one embodiment, the composition comprises a rheology modifier to increase the substantivity of the composition, such that it does not drip undesirably onto other areas of the body, onto clothing, or onto home furnishings and may also perform as a film former, thereby increasing the delivery of apigenin to the hair follicle and surrounding tissue. Any suitable rheology modifier can be used, for example, a cellulose-based rheology modifier, such as hydroxypropylmethylcellulose. Other non-limiting examples of rheology modifiers include acrylamide/ammonium acrylate copolymer (and) polyisobutene (and) polysorbate 20; acrylamide/sodium acryloyldimethyl taurate copolymer/isohexadecane/polysorbate 80; acrylates copolymer; acrylates/beheneth-25 methacrylate copolymer; acrylates/C10-C30 alkyl acrylate crosspolymer; acrylates/steareth-20 itaconate copolymer; ammonium polyacrylate/Isohexadecane/PEG-40 castor oil; C12-16 alkyl PEG-2 hydroxypropylhydroxyethyl ethylcellulose (HM-EHEC); carbomer; crosslinked polyvinylpyrrolidone (PVP); dibenzylidene sorbitol; hydroxyethyl ethylcellulose (EHEC); hydroxypropyl methylcellulose (HPMC); hydroxypropyl methylcellulose (HPMC); hydroxypropylcellulose (HPC); methylcellulose (MC); methylhydroxyethyl cellulose (ME-HEC); PEG-150/decyl alcohol/SMDI copolymer; PEG-150/stearyl alcohol/SMDI copolymer; polyacrylamide/C13-14 isoparaffin/laureth-7; polyacrylate 13/polyisobutene/polysorbate 20; polyacrylate crosspolymer-6; polyamide-3; polyquaternium-37 (and) hydrogenated polydecene (and) trideceth-6; polyurethane-39; sodium acrylate/acryloyldimethyltaurate/dimethylacrylamide; crosspolymer (and) isohexadecane (and) polysorbate 60; sodium polyacrylate. Exemplary commercially-available rheology modifiers include ACULYN™ 28, Klucel M CS, Klucel H CS, Klucel G CS, SYLVACLEAR AF1900V, SYLVACLEAR PA1200V, Benecel E10M, Benecel K35M, Optasense RMC70, ACULYN™33, ACULYN™46, ACULYN™22, ACULYN™44, Carbopol Ultrez 20, Carbopol Ultrez 21, Carbopol Ultrez 10, Carbopol 1342, Sepigel™ 305, Simulgel™600, Sepimax Zen, and combinations thereof.

The formulations of the present invention may be present in typical hair care compositions. They may be in the form of solutions, dispersion, emulsions, powders, talcs, encapsulated, spheres, spongers, solid dosage forms, foams, and other delivery mechanisms. The composition of the present invention may be hair tonics, leave-on hair products such as conditioners, treatment, and styling products, rinse-off hair products such as conditioners, shampoos, and treatment products; and any other form that may be applied to the hair and preferably applied to the scalp.

As disclosed herein, the hair care composition contains apigenin. In embodiments where one or more indole compounds, one or more xanthine compounds, one or more vitamin $B_3$ compounds, and/or one or more panthenol compounds are present, the apigenin may be in the a single phase or a single product, or the apigenin may be in a separate phase or separate product. If two products are used, the products may be used together, at the same time or sequentially. Sequential use may occur in a short period of time, such as immediately after the use of one product, or it may occur over a period of hours or days.

According to one embodiment, the hair care composition includes greater than 0.005% to about 5% apigenin; from about 0.15% to about 12% of the solubilizing agent; at least about 20% of the aqueous carrier; and further includes from about 0% to about 5% of the conditioning agent; from about 0% to about 5% of the moisturizing agent; from about 0% to about 10% of the penetrant agent; from about 0% to about 50% of the organic solvent; from about 0% to about 10% of the neutralizing agent; from about 0% to about 20% of the rheology modifier; from about 0% to about 20% of the surfactant; from about 0% to about 3% of the fragrance agent; from about 0 wt % to about 3 wt % of the aesthetics enhancer, or from about 0 wt % to about 10 wt % of the partitioning agent. According to another embodiment, the hair care composition further includes further includes from about 0.1% to about 5% of the conditioning agent; from about 0.5% to about 5% of the moisturizing agent; from about 0.05% to about 10% of the penetrant agent; from about 0.5% to about 50% of the organic solvent; from about 0.1% to about 10% of the neutralizing agent; from about 0.5% to about 20% of the rheology modifier; from about 0.1% to about 20% of the surfactant; from about 0.1% to about 3% of the fragrance agent; from about 0.1% to about 3% of the aesthetics enhancer, or from about 0.1% to about 10% of the partitioning agent.

B. Method of Making the Hair Care Compositions

According to another embodiment of the invention, a process for preparing a hair care composition includes mixing apigenin and a solubilizing agent at a temperature sufficient to allow dissolution of the apigenin in the solubilizing agent to form a premixture; combining the premixture with an aqueous carrier to form the hair care composition; and optionally, adjusting the pH of the hair care composition with acid to within a range from about 3 to about 10. The premixture is prepared by combining apigenin and one or more solubilizing agents. Solubilization energy (e.g., stiffing, sonication, milling, heat, etc.) may be applied to accelerate the dissolution process. For example, a premixture of apigenin in triethanolamine may be prepared by combining apigenin and triethanolamine in a single vessel and heating the mixture to 70° C. while stirring until a clear solution results. According to one aspect of the exemplary method of making the premixture, the combined apigenin and triethanolamine are mixed at 50-100 rpm using a IKA RET CV-S1 mixer. According to another aspect, the combination is mixed at 300-500 rpm using a IKA Eurostar PWR CV-S1 mixer.

According to one aspect of the method, the weight ratio of apigenin to solubilizing agent ranges from about 1:50 to about 1:4. For example, the weight ratio may be about 1:45, about 1:40, about 1:35, about 1:30, about 1:25, about 1:20, about 1:15, about 1:10, about 1:8, about 1:5, or within a range between the recited values. The weight of the solubilizing agent includes the weight of all the solubilizing agents used in making the premixture.

According to another aspect, the pH is adjusted to the desired value within the range from about 3 to about 10 using an acid. For example, the pH may be about 4, about 5, about 6, about 7, about 8, about 9, or within a range between the recited values. According to one embodiment, the pH is adjusted with an acid to within a range from about 6.5 to about 9. Exemplary acids include carboxylic acids, such as citric acid, and mineral acids, such as hydrochloric acid.

According to another aspect, the method further includes adding a rheology modifier to the hair care composition to obtain a rheology value in the range from about 30 cPs to about 50,000 cPs. For example, the rheology value may be about 50 cPS, about 100 cPs, about 300 cPs, about 500 cPs, about 1,000 cPs, about 10,000 cPs, about 25,000 cPs, or within a range between the recited values. Exemplary rheology modifiers include those available under the tradenames ACULYN™ 28, Klucel M CS, Klucel H CS, Klucel G CS, SYLVACLEAR AF1900V, SYLVACLEAR PA1200V, Benecel E10M, Benecel K35M, Optasense RMC70, ACULYN™33, ACULYN™46, ACULYN™22, ACULYN™44, Carbopol Ultrez 20, Carbopol Ultrez 21, Carbopol Ultrez 10, Sepigel™ 305, Simulgel™600, Sepimax Zen, Carbopol 1342, and combinations thereof.

C. Method for Increasing the Appearance of Thicker and Fuller Hair and/or Delaying the Appearance of Gray Hair According to yet another embodiment of the present invention, a method is provided for increasing the diameter of the hair shaft and follicle; increasing the density of hair follicles; and/or delaying the appearance of gray hair. This may lead to an appearance of thicker and/or fuller hair and may lead to the appearance of delayed onset of gray hair. In one aspect, the method comprises applying the hair care composition to a skin surface from which a region of hair grows. For instance, the hair care composition can be applied to the scalp. In another embodiment, the method comprises topically applying a hair care composition comprising an effective amount of apigenin to a region of skin of a mammal seeking to increase the appearance of thicker and/or fuller hair or delaying the appearance of gray hair.

In still another embodiment, the method comprises applying the composition according to a regimen, wherein said regimen comprises:

(a) cleansing the scalp to form a cleansed scalp;

(b) topically applying the composition to said cleansed scalp.

The hair care composition may be used daily, weekly, or in a variety of regimens. The hair care composition may be used more than once a day, such as at night and in the morning. The product may be used after washing the hair (also on wet or dry hair), which may mean using the composition more than once per day on certain days or use only a few times per week. The hair care composition may be used three times per day, twice per day, once per day, six times per week, five times per week, four times per week, three times per week, two times per week, or one time per week. In some embodiments, the hair care composition is used four, five, six or seven times per week.

The hair care composition may be used by males and females. The hair care composition may be desired to be used by individuals who desire to promote hair growth or have healthier or younger looking hair. For example, the hair care composition may be used on subjects who have no diagnosed hair loss. The hair care composition may be used on subjects having an age of greater than about 20, 25, 30, 35, 40, 45, or 50. The hair care composition may be used on subjects having an age of less than about 70, 65, 60, 55, or 50. Accordingly, the hair care composition may be used on subjects between the ages of about 20-70, from about 30-60, and from about 35-55. Hair diameter may start to decrease after age 20 so healthier hair and increased appearance of fuller and thicker hair may be desired after these ages. Hair diameter continues to decrease and in some subject to a greater extent after age 30 or 40. Additionally, gray hair begins to emerge as early as age 20 but more commonly after age 30 or 40 depending upon genetics.

FORMULATIONS AND EXAMPLES

The following are non-limiting examples of the present invention. The examples are given solely for the purpose of illustration and are not to be construed as limitations of the present invention, as many variations thereof are possible without departing from the spirit and scope of the invention, which would be recognized by one of ordinary skill in the art.

In the examples, all concentrations are listed as weight percent, unless otherwise specified and may exclude minor materials such as diluents, filler, and so forth. The listed formulations, therefore, comprise the listed components and any minor materials associated with such components. As is apparent to one of ordinary skill in the art, the selection of these minors will vary depending on the physical and chemical characteristics of the particular ingredients selected to make the present invention as described herein. Triethanolamine is abbreviated TEA.

TABLE 3

Exemplary results of preparing apigenin premixtures with various solubilizing agents.

| Solubilizing Agent | Temperature (° C.) | Mixing Speed (rpm) | Solubility (mg/ml) |
|---|---|---|---|
| 1-Dimethylamino-2-propanol | room temp | 300 | 9.50 |
| 1-Dimethylamino-2-propanol | room temp | 300 | 20.18 |
| 1-Dimethylamino-2-propanol solution | room temp | 300 | 20.20 |
| 1-Dimethylamino-2-propanol solution | room temp | 1500 sm | 20.00 |
| 1-Dimethylamino-2-propanol/Ethanolamine | room temp | 300 | 16.56 |
| 1-Dimethylamino-2-propanol/Ethanolamine/TEA | room temp | 300-500 | 16.48 |
| 1-Dimethylamino-2-propanol/Ethylenediamine | room temp | 400-600 | 20.06 |
| 1-Dimethylamino-2-propanol/TEA | room temp | 300-810 | 17.28 |
| 1-Methylimidazole | 82 | 100 | 20.45 |
| 2-Dimethylaminoethanol | 29 | 300 | 19.95 |
| 2-Dimethylaminoethanol | room temp | 300 | 20.15 |
| 2-amino-2-methyl-1-propanol | 71 | 450 | 14.83 |
| 2-amino-2-methyl-1-propanol | 71 | 400 | 20.03 |
| Diethanolamine | 128 | 550 | 20.25 |
| Ethanolamine | 76 | 300 | 20.31 |
| Ethanolamine | room temp | 350-740 | 20.20 |
| Ethanolamine | 29 | 350-500 | 20.13 |
| Ethanolamine/TEA | 29 | 300-600 | 18.01 |
| Ethanolamine/TEA | room temp | 350-500 | 15.95 |
| Ethylenediamine | 28 | 320 | 20.03 |
| Ethylenediamine | room temp | 320 | 20.15 |
| Laurocapram, 98% | 140 | 500-600 | 14.03 |
| Laurocapram, 98% | room temp | 500-600 | 13.90 |
| N-Methylformamide | 101 | 400 | 13.65 |
| Pyridine | room temp | 300 | 15.75 |
| Synthetic Apigenin in Ethanolamine | 76 | 400 | 20.17 |
| Synthetic Apigenin in TEA | 169 | 450 | 14.72 |
| TEA | room temp | 450-590 | 20.04 |
| TEA/1-Dimethylamino-2-propanol | room temp | 350-450 | 17.01 |
| TEA/1-Dimethylamino-2-propanol/Ethylenediamine | room temp | 330-600 | 20.59 |
| TEA/2-Dimethylaminoethanol/1-Dimethylamino-2-propanol | room temp | 330-400; 1500 sm | 15.00 |
| TEA/2-Dimethylaminoethanol/1-Dimethylamino-2-propanol | room temp | 1500 sm | 15.00 |
| TEA/2-Dimethylaminoethanol/1-Dimethylamino-2-propanol | room temp | 1500 sm | 15.00 |
| Triethylene glycol | 156 | 300 | 6.11 |
| Dimethyl capramide | Room temp | 400 | 16.00 |
| Triethylenamine | | | |
| TEA/Dimethyl capramide | | | |
| TEA/Triethylenamine | | | |

Exemplary additives, which are used in preparing exemplary formulations of the hair care compositions in accordance with embodiments of the present invention, are provided in Table 4.

TABLE 4

Exemplary components for the hair care compositions.

| Entry | Ingredients | Role | Concentrations | Range |
|---|---|---|---|---|
| 1 | Ethanol | alcohol/solvent | 20%, 21%, 50%, 57%, 70% | 20-80% |
| 2 | Water | carrier | QS | QS |
| 3 | Tween 80 | nonionic surfactant | 0%, 2.5%, 5%, 10% | 0-10% |
| 4 | Hydrolite-5 | alcohol/solvent | 0%, 2.5%, 5%, 10% | 0-10% |
| 5 | Dipropylene Glycol (DPG) | alcohol/solvent | 0%, 5%, 50% | 0-50% |
| 6 | Arlasolve DMI (dimethyl isosorbide) | high purity solvent | 0%, 8% | 0-8% |
| 7 | Apigenin | anti-inflammatory | 0.32%, 0.50%, 1% | <1-1% |
| 8 | Triethanolamine | solvent/ neutralizer | 0%, 1.30%, 1.89%, 2.44%, 2.46%, 3.99%, 19%, 9.50%, 11.50%, 12.26% | <4.00% |
| 9 | Citric Acid | Neutralizer | 0-3% | <3% |
| 10 | Eastman DE Solvent (Transcutol - Diethylene glycol monoethyl ether) | solvent | 10% | 0-30% |
| 11 | Eldew SL-205 | solvent | 50% | 0-60% |
| 12 | SF 1202 Silicone fluid | moisturizer | 19% | 0-50% |

TABLE 4-continued

Exemplary components for the hair care compositions.

| Entry | Ingredients | Role | Concentrations | Range |
|---|---|---|---|---|
| 13 | PEG 10 Dimethicone | moisturizer | 1% | 0-3% |
| 14 | Vitamin E Acetate | skin penetration enhancement, moisturizer | 0.50% | 0-3% |
| 15 | Hexylene Glycol | skin penetration enhancement | 5% | 0-10% |
| 16 | Oleic Acid | skin penetration enhancement | 1% | 0-5% |
| 17 | Panthenol | conditioning agent | 0.15% | 0-5% |
| 18 | Niacinamide | conditioning agent | 2.50% | 0-25% |
| 19 | Caffeine | conditioning agent | 0.75% | 0-10% |
| 20 | Wakana HE | Fragrance | 1% | 0-5% |
| 21 | ACULYN™28 | rheology modifier | 1.25%, 2.5%, 3.75%, 5%, 7.5%, 10%, 12.5%, 17.5% | 0.10-17.5% |

Other exemplary partitioning agents, such as triethylene glycol (0-10%), propylene carbonate (0-10%), or hexylene glycol (0-10%); and other penetration enhancers, such as oleic Acid (0-5%) or vitamin E Acetate (0-1%).

To prepare the hair care compositions using the premixture of apigenin and the solubilizing agent, exemplary order of mixing of the ingredients and the premixture are provide in Table 5, wherein reference to the ingredients in the Order of Addition is with respect to the entry numbers of Table 4.

TABLE 5

Exemplary mixing methods for preparing the hair care compositions.

| Entry | Order of Addition | Mixing Steps |
|---|---|---|
| A | 2, 21, 1, 8 + 7, 20, 9, 2 | IKA Overhead mixer and/or High speed mixer |
| B | 2, 21, 1, 8 + 7, 20, 17, 18, 19, 9, 2 | IKA Overhead mixer and/or High speed mixer |
| C | 2, 21, 1, 8 + 7, 15, 14, 16, 20, 9, 2 | IKA Overhead mixer and/or High speed mixer |
| D | 2, 21, 1, 8 + 7, 13, 20, 9, 2 | IKA Overhead mixer and/or High speed mixer |
| E | 2, 21, 5, 6, 4, 3, 8 + 7 | IKA Overhead mixer and/or High speed mixer |
| F | 2, 1, 21, 8 + 7, 3, 9, 2 | IKA Overhead mixer and/or High speed mixer |
| G | 4, 2, 3, 6, 7, 1, 21 | IKA Overhead mixer |
| H | 2, 3, 21, 8 + 7, 1, 9, 2 | IKA Overhead mixer and/or High speed mixer |
| I | 2, 1, 8 + 7, 9, 2 | IKA Overhead mixer and/or High speed mixer |
| J | 2, 1, 3, 8 + 7, 9, 2 | IKA Overhead mixer and/or High speed mixer |
| K | 2, 21, 1, 8 + 7, 9, 2 | IKA Overhead mixer and/or High speed mixer |
| L | 2, 21, 8 + 7, 1, 3, 9, 2 | IKA Overhead mixer and/or High speed mixer |
| M | 8 + 7, 2, 1, 5, 6, 4, 3 | IKA Overhead mixer |
| N | 1, 7, 10, 11, 12 | IKA Overhead mixer |

In Vitro Skin Penetration General Protocol

In vitro skin penetration of actives, such as apigenin, from topically applied formulations is determined using the Franz diffusion cell assay. The method is widely used in the skin care industry for assessment of skin penetration and for the dermal absorption safety assessments. See Franz, T. J. *Percutaneous absorption. On the relevance of in vitro data.* J. Invest. Dermatol. 64: 190-195, 1975; Franz, et al. *The use of excised human skin to assess the bioequivalence of topical products.* Skin Pharmacol. Physiol. 22: 276-286, 2009; and OECD Guideline (#428) for the Testing of Chemicals, Adopted 13 Apr., 2004. A diffusion assay method is described in general below:

Split-thickness human cadaver skin (Allosource, Englewood, Colo.) or dermatomed pig skin is thawed at ambient conditions, cut into appropriately sized sections, and then mounted in standard Franz-type diffusion cells (0.79 cm$^2$ surface area) maintained at about 37° C. The receptor compartments [~5 mL] are filled with phosphate buffered saline (PBS—pH 7.4) that included 1% polysorbate-20 and 0.02% sodium azide, and the skin is allowed to equilibrate for two hours. The cells are randomized to treatment based upon $^3$H$_2$O flux through the mounted skin (150 μL of $^3$H20 applied for five minutes and removed). Diffusion cells are randomized by ranking each cell according to water flux and distributing cells across treatment legs such that each group includes cells across the range of observed water flux. Each treatment group typically has 6 replicates.

Aliquots of the test products/formulations are spiked with the appropriate radioactive material (i.e. $^{14}$C-niacinamide) with approximately 3 μCi per 300 mg product aliquot, mixed and assayed for total radioactivity in triplicate using Ultima Gold [Perkin-Elmer] liquid scintillation cocktail (LSC) and liquid scintillation counting (Tri-Carb 2500 TR Liquid Scintillation Analyzer, PerkinElmer, Boston, Mass.).

Skin is topically dosed with 5 μL of product using a positive displacement pipette. The product is gently spread over the surface of the skin (0.79 cm$^2$) using the pipet tip. The receptor solution is collected and replaced at various time points following application (i.e. 2, 4 and 6 hrs) with a final collection at 24 hrs. Skin is also collected at (6 hours if specified) and 24 hours post-application. After the final receptor collection for each study leg, each skin sample is wiped two times with Whatman filter paper soaked with PBS/Tween 20 and once with 70%/30% ethanol/water to remove unabsorbed (residual) product. The epidermis is separated from the residual dermis by dissection. The skin sections are dissolved in 0.50-1.25 mL Soluene-350 (Perkin Elmer, Boston, Mass.) at 50° C. overnight, and all receptor collections, filter paper wipes, and solubilized tissue sections are counted using liquid scintillation counting as described previously. In experiments where radioactive tracers are not available, analytical methods, such as LCMS, are developed for the active material of interest.

Disintegrations-per-minute (DPMs) for each compartment of each cell are blank corrected and summed to obtain a total recovered radiolabel value for a given cell. The DPMs of each compartment are then normalized to the total recovered radiolabel value to obtain a "percent recovered radiolabel" parameter for each compartment (individual receptor collections, epidermis, dermis, and wipes for mass balance). Cumulative receptor values to each collection time point are calculated as the sum of the individual collections to that time point, with the total receptor value as the sum of all individual collections. The total skin value is the sum of the epidermis (including stratum corneum) and dermis values, and the total permeated value the sum of total skin and cumulative receptor values. Skin penetration data are typically expressed as % of applied dose, % of recovered dose (normalized for mass balance) and/or ug/cm$^2$.

Samples, in accordance with an embodiment of the invention, can be prepared and tested using the in vitro skin penetration protocol described above. Sample A includes 0.32 wt % apigenin, 50 wt % ethanol, 7.5 wt % Aculyn™ 28, 38.72 wt % water, 2.46 wt % triethanolamine, 1 wt % Wakana HE, and 0.75 wt % citric acid, and has a pH of 7.0. Sample B includes 1 wt % apigenin, 50 wt % ethanol, 7.5 wt % Aculyn™ 28, 32.8 wt % water, 7.7 wt % triethanolamine, 1 wt % Wakana HE, and 2.42 wt % citric acid, and has a pH of 7.2. Comparative Sample includes 1 wt % apigenin, 20 wt % ethanol, 10 wt % Hydrolite®-5, 50 wt % dipropyleneglycol, 10 wt % Tween 80, 8 wt % Arlasolve™ DMI PC, and 1 wt % Klucel, and has a pH of 7.0.

Figure 1:
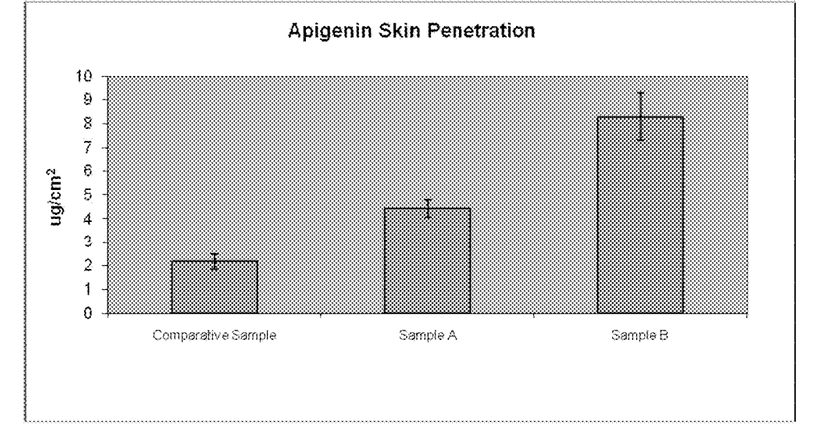
FIG. 1 is a chart showing comparative skin penetration results of several hair care compositions in accordance with an embodiment of the present invention.

Table 6 demonstrates that apigenin-containing compositions of the present invention provide enhanced skin penetration compared with known compositions using traditional solubilizing agents.

TABLE 6

Comparative Skin Penetration data of various hair care compositions.

| | Comparative Sample | Sample A | Sample B |
|---|---|---|---|
| Mean | 2.18 | 4.42 | 8.30 |
| sem | 0.32 | 0.37 | 0.98 |

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

All documents cited in the Detailed Description of Embodiments of the Invention are, in relevant part, incorporated herein by reference; the citation of any document is not to be construed as an admission that it is prior art with respect to the present invention. To the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A process for preparing a hair care composition comprising:
    a) mixing from about 0.15 wt % apigenin, based on the total composition, and from about 1 wt % to about 12 wt % of a triethanolamine, based on the total composition, at a temperature sufficient to allow dissolution of the apigenin in the triethanolamine to form a premixture, wherein the weight ratio of apigenin to the triethanolamine ranges from about 1:50 to about 1:4;
    b) combining the premixture with an aqueous carrier to form the hair care composition; and
    c) adjusting a pH of the hair care composition with an acid to within a range from about 3 to about 10.

2. The process of claim 1, wherein the weight ratio of apigenin to the triethanolamine is within the range from about 1:10 to about 1:4.

3. The process of claim 1, further comprising
    d) adding a rheology modifier to the hair care composition to obtain a rheology value in the range from about 30 cPs to about 50,000 cPs.

4. The process of claim 3, wherein the rheology value is in the range from about 300 to about 5,000 cPs.

5. The process of claim 3, wherein the rheology modifier is selected from the group consisting of hydroxypropylmethylcellulose; a mixture of acrylamide/ammonium acrylate copolymer, polyisobutene, and polysorbate 20; acrylamide/sodium acryloyldimethyl taurate copolymer/isohexadecane/polysorbate 80; acrylates copolymer; acrylates/beheneth-25 methacrylate copolymer; acrylates/C10-C30 alkyl acrylate crosspolymer; acrylates/steareth-20 itaconate copolymer; ammonium polyacrylate/Isohexadecane/PEG-40 castor oil; C12-16 alkyl PEG-2 hydroxypropylhydroxyethyl ethylcellulose (HM-EHEC); carbomer; crosslinked polyvinylpyrrolidone (PVP); dibenzylidene sorbitol; hydroxyethyl ethylcellulose (EHEC); hydroxypropyl methylcellulose (HPMC); hydroxypropyl methylcellulose (HPMC); hydroxypropylcellulose (HPC); methylcellulose (MC); methylhydroxyethyl cellulose (MEHEC); PEG-150/decyl alcohol/SMDI copolymer; PEG-150/stearyl alcohol/SMDI copolymer; polyacrylamide/C13-14 isoparaffin/laureth-7; polyacrylate 13/polyisobutene/polysorbate 20; polyacrylate crosspolymer-6; polyamide-3; polyquaternium-37 (and) hydrogenated polydecene (and) trideceth-6; polyurethane-39; sodium acrylate/acryloyldimethyltaurate/dimethylacrylamide; crosspolymer (and) isohexadecane (and) polysorbate 60; sodium polyacrylate and combinations thereof.

6. The process of claim 1, wherein the pH of the hair care composition is adjusted with an acid to within a range from about 6.5 to about 9, and wherein the acid is citric acid or hydrochloric acid.

* * * * *